United States Patent
Kasahara (10) Patent No.: US 7,440,797 B2
(45) Date of Patent: Oct. 21, 2008

(54) ABDOMINAL IMPEDANCE BASED BODY COMPOSITION METER

(75) Inventor: Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/882,345

(22) Filed: Aug. 1, 2007

(65) Prior Publication Data

US 2008/0071186 A1    Mar. 20, 2008

(30) Foreign Application Priority Data

Sep. 19, 2006   (JP) .............................. 2006-253242

(51) Int. Cl.
*A61B 5/05*   (2006.01)
(52) U.S. Cl. .................................... 600/547
(58) Field of Classification Search ................. 600/547
See application file for complete search history.

(56) References Cited

U.S. PATENT DOCUMENTS

| 6,354,996 B1 | 3/2002 | Drinan et al. |
| 2003/0097081 A1 | 5/2003 | Masuda et al. |
| 2005/0090760 A1 * | 4/2005 | Kobayashi ................... 600/547 |
| 2005/0222516 A1 | 10/2005 | Kasahara et al. |
| 2006/0025701 A1 | 2/2006 | Kasahara |

FOREIGN PATENT DOCUMENTS

| EP | 1 464 277 A2 | 10/2004 |
| EP | 1 844 707 A1 | 10/2007 |
| JP | 2004-135698 | 5/2004 |
| JP | 2005-288023 | 10/2005 |
| JP | 2006-61677 | 3/2006 |

OTHER PUBLICATIONS

European Search Report, issued in European Patent Application No. 07017152.5-2319, dated on Jan. 21, 2008.

* cited by examiner

*Primary Examiner*—Max Hindenburg
*Assistant Examiner*—Emily M Lloyd
(74) *Attorney, Agent, or Firm*—McDermott Will & Emery LLP (57) ABSTRACT

An abdominal impedance based body composition meter is provided for estimating a body composition indicator with high accuracy. In one embodiment, the body composition meter measures pressing forces while load detection sections 3a-3d are pressed against the abdomen and abdominal impedances are measured by electrodes 2a-2d. Body composition indicators are estimated based on the measured pressing forces and the abdominal impedances.

5 Claims, 8 Drawing Sheets

ATTACH ELECTRODES TO ABDOMEN AND PRESS MEASUREMENT SWITCH.

FIG. 5B

MEASURING IMPEDANCE ...

FIG. 5C

| VISCERAL FAT TYPE ! | |
|---|---|
| VISCERAL FAT | 100cm² |
| SUBCUTANEOUS FAT | 50cm² |
| BODY FAT PERCENTAGE | 20.3% |
| TRUNCAL FAT PERCENTAGE | 20.5% |

FIG. 5D

| SUBCUTANEOUS FAT TYPE ! | |
|---|---|
| VISCERAL FAT | 50cm² |
| SUBCUTANEOUS FAT | 100cm² |
| BODY FAT PERCENTAGE | 20.3% |
| TRUNCAL FAT PERCENTAGE | 20.5% |

FIG. 5E

DO YOU WANT TO MAKE MEASUREMENTS AGAIN ?

ABDOMINAL IMPEDANCE BASED BODY COMPOSITION METER

BACKGROUND OF THE INVENTION (i) Field of the Invention

This invention relates to an abdominal impedance based body composition meter which measures an impedance in the abdomen (abdominal impedance) and estimates a body composition indicator.

(ii) Description of the Related Art

In the technology of estimating indicators (such as amount, thickness, area and percentage) associated with body compositions (such as fat, muscles, bones and other tissues constituting a body), since introduction of a body fat meter which measures an impedance occurring between both feet, between both hands or between a hand and a foot and estimates the body fat percentage of the whole body which is a body composition indicator in the market, research and development on estimation of indicators for further health management have been made, resulting in development and introduction of a body fat meter which measures an impedance in the abdomen and estimates a subcutaneous fat amount or visceral fat amount in the abdomen which is a body composition indicator.

A body fat measuring device disclosed in Patent Literature 1 and a body composition meter disclosed in Patent Literature 2 comprise support means having a plurality of electrodes disposed on a surface thereof and measure an abdominal impedance and estimate a body composition indicator by pressing the electrode-disposed surface of the support means against the abdomen, passing a current between current-passing electrodes out of the above electrodes and detecting a voltage generated in the abdomen upon passage of the current between measuring electrodes out of the above electrodes.

Patent Literature 1

Japanese Patent Application Laid-Open No. 288023/2005

Patent Literature 2

Japanese Patent Application Laid-Open No. 61677/2006

However, in the case of the devices disclosed in Patent Literatures 1 and 2, when the support means is pressed against the abdomen, the state of deformation of the abdomen varies according to the pressing force. That is, when the force pressing the support means against the abdomen is large, the electrodes are pressed into the abdomen deeply, while when the force pressing the support means against the abdomen is small, the electrodes are pressed into the abdomen shallowly. When the state of deformation of the abdomen varies, the state of current-passing part also varies. That is, the electrical impedance of the current-passing part varies. Therefore, there is a problem that an abdominal impedance measured varies according to the strength of the force pressing the support means against the abdomen.

The present invention has been conceived to solve the above problem of the prior art, and an object of the present is to provide an abdominal impedance based body composition meter capable of estimating a body composition indicator with high accuracy.

SUMMARY OF THE INVENTION

An abdominal impedance based body composition meter of the present invention comprises:
abdominal impedance measuring means,
pressing force measuring means, and
body composition estimating means, wherein the abdominal impedance measuring means comprises a plurality of electrodes and a support which keeps the electrodes pressed against the abdomen and measures an abdominal impedance when the electrodes are in contact with the abdomen, the pressing force measuring means measures a pressing force when the electrodes are pressed against the abdomen by the support, and the body composition estimating means estimates a body composition indicator based on the abdominal impedance measured by the abdominal impedance measuring means and the pressing force measured by the pressing force measuring means.

Further, the electrodes comprise a pair of current-passing electrodes and a pair of measuring electrodes, the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, the abdominal impedance measuring means determines an abdominal impedance based on a potential difference which is detected between the measuring electrodes when a low-frequency current is passed between the current-passing electrodes and determines an abdominal impedance based on a potential difference which is detected between the measuring electrodes when a high-frequency current is passed between the current-passing electrodes, and the body composition estimating means computes and estimates an abdominal total fat area as the body composition indicator by substituting the abdominal impedance determined by the abdominal impedance measuring means by passing the low-frequency current into $Z_{low}$, the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$ and constants which provide a correlation with an abdominal total fat area determined by a standard technique into a, b, c and d in an arithmetic expression represented by abdominal total fat area=$a \times Z_{low} + b \times Z_{high} + c \times SI_{avg} + d \times SV_{avg}$.

Further, the electrodes comprise a pair of current-passing electrodes and a pair of measuring electrodes, the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, the abdominal impedance measuring means determines an abdominal impedance based on a potential difference which is detected between the measuring electrodes when a low-frequency current is passed between the current-passing electrodes and determines an abdominal impedance based on a potential difference which is detected between the measuring electrodes when a high-frequency current is passed between the current-passing electrodes, and the body composition estimating means computes and estimates a subcutaneous fat area as the body composition indicator by substituting the abdominal impedance determined by the abdominal impedance measuring means by passing the low-frequency current into $Z_{low}$, the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$ and constants which provide a correlation with a subcutaneous fat area determined by a standard technique into e, f, g and h in an arithmetic expression represented by subcutaneous fat area=$e \times Z_{low} - f \times Z_{high} + g \times SI_{avg} + h \times SV_{avg}$.

Further, the electrodes comprise a pair of current-passing electrodes and a pair of measuring electrodes, the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, the abdominal impedance measuring means determines an abdominal impedance based on a potential difference which is detected between the measuring electrodes when a low-frequency current is passed between the current-passing electrodes and determines an abdominal impedance based on a potential difference which is detected between the measuring electrodes when a high-frequency current is passed between the current-passing electrodes, and the body composition estimating means computes and estimates a visceral fat area as the body composition indicator by substituting the abdominal impedance determined by the abdominal impedance measuring means by passing the low-frequency current into $Z_{low}$, the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$ and constants which provide a correlation with a visceral fat area determined by a standard technique into i, j, k and m in an arithmetic expression represented by visceral fat area=$-i \times Z_{low} + j \times Z_{high} + k \times SI_{avg} + m \times SV_{avg}$.

Further, the electrodes comprise a pair of current-passing electrodes and a pair of measuring electrodes, the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, the abdominal impedance measuring means determines an abdominal impedance based on a potential difference which is detected between the measuring electrodes when a high-frequency current is passed between the current-passing electrodes, and the body composition estimating means computes and estimates a truncal fat percentage as the body composition indicator by substituting the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$ and constants which provide a correlation with a truncal fat percentage determined by a standard technique into n, p, q and r in an arithmetic expression represented by truncal fat percentage=$n - p \times 1 \div Z_{high} + q \times SI_{avg} + r \times SV_{avg}$.

Further, the electrodes comprise a pair of current-passing electrodes and a pair of measuring electrodes, the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, the abdominal impedance measuring means determines an abdominal impedance based on a potential difference which is detected between the measuring electrodes when a high-frequency current is passed between the current-passing electrodes, and the body composition estimating means computes and estimates a total body fat percentage as the body composition indicator by substituting the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$ and constants which provide a correlation with a total body fat percentage determined by a standard technique into n, p, q, r, s and t in an arithmetic expression represented by total body fat percentage=$s \times (n - p \times 1 \div Z_{high} + q \times SI_{avg} + r \times SV_{avg}) + t$.

The abdominal impedance based body composition meter of the present invention measures pressing forces by the pressing force measuring means and estimates body composition indicators based on the measured pressing forces and abdominal impedances measured by the abdominal impedance measuring means by the body composition estimating means. Therefore, even if abdominal impedances measured by the abdominal impedance measuring means vary due to a difference in the degree of impression of the electrodes into the abdomen which is caused by a variation in force pressing the support, body composition indicators can be obtained with high accuracy.

Further, in particular, since the abdominal impedance based body composition meter of the present invention calculates an abdominal total fat area, subcutaneous fat area, visceral fat area, truncal fat percentage and total body fat percentage as body composition indicators by use of the arithmetic expressions which take the pressing forces $SI_{avg}$ and $SV_{avg}$ into consideration and provide correlations with body composition indicators determined by a standard technique, the body composition indicators can be obtained securely with high accuracy.

BRIEF DESCRIPTION OF THE DRAWINGS

FIG. 1 shows external views of an abdominal impedance based body composition meter according to the present invention wherein 1A is a front view and 1B is a plan view.

DETAILED DESCRIPTION OF THE PREFERRED EMBODIMENTS

An abdominal impedance based body composition meter according to the present invention comprises abdominal impedance measuring means, pressing force measuring means and body composition estimating means.

The abdominal impedance measuring means comprises a plurality of electrodes and a support which keeps these electrodes pressed against the abdomen and measures an abdominal impedance when these electrodes are in contact with the abdomen.

The pressing force measuring means measures a pressing force when the electrodes are pressed against the abdomen by the support.

The body composition estimating means estimates a body composition indicator, based on the abdominal impedances measured by the abdominal impedance measuring means and the pressing forces measured by the pressing force measuring means.

According to the thus constituted abdominal impedance based body composition meter, a force pressing the support is obtained in the pressing force measuring means, and a body composition indicator based on this pressing force is estimated in the body composition estimating means. Hence, even if abdominal impedances measured by the abdominal impedance measuring means vary due to a difference in the degree of impression of the electrodes into the abdomen which is caused by a variation in force pressing the support, body composition indicators can be estimated with high accuracy.

Hereinafter, an embodiment based on the above form will be described specifically.

EXAMPLES

Figure 1A:
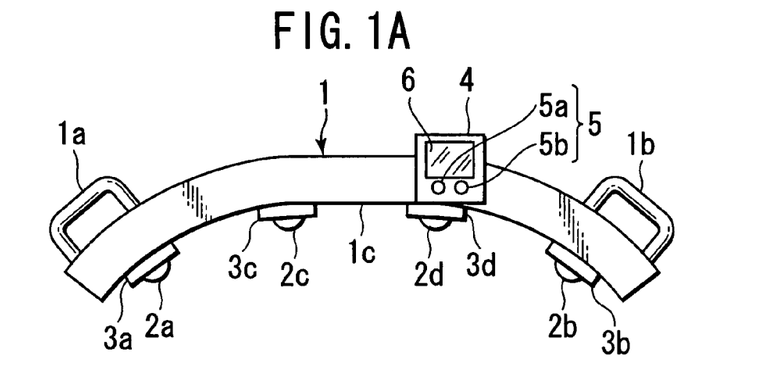
Figure 1B:
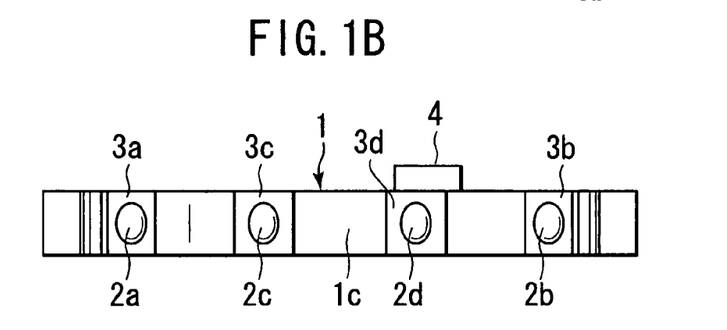
Figure 2:
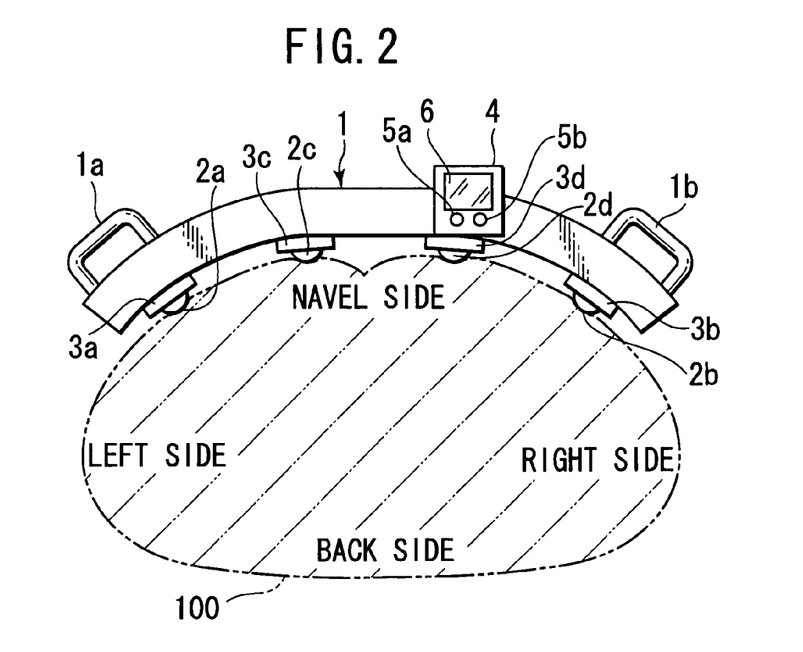
FIG. 2 is a diagram illustrating a state of making a measurement by use of the abdominal impedance based body composition meter according to the present invention.
Figure 3:
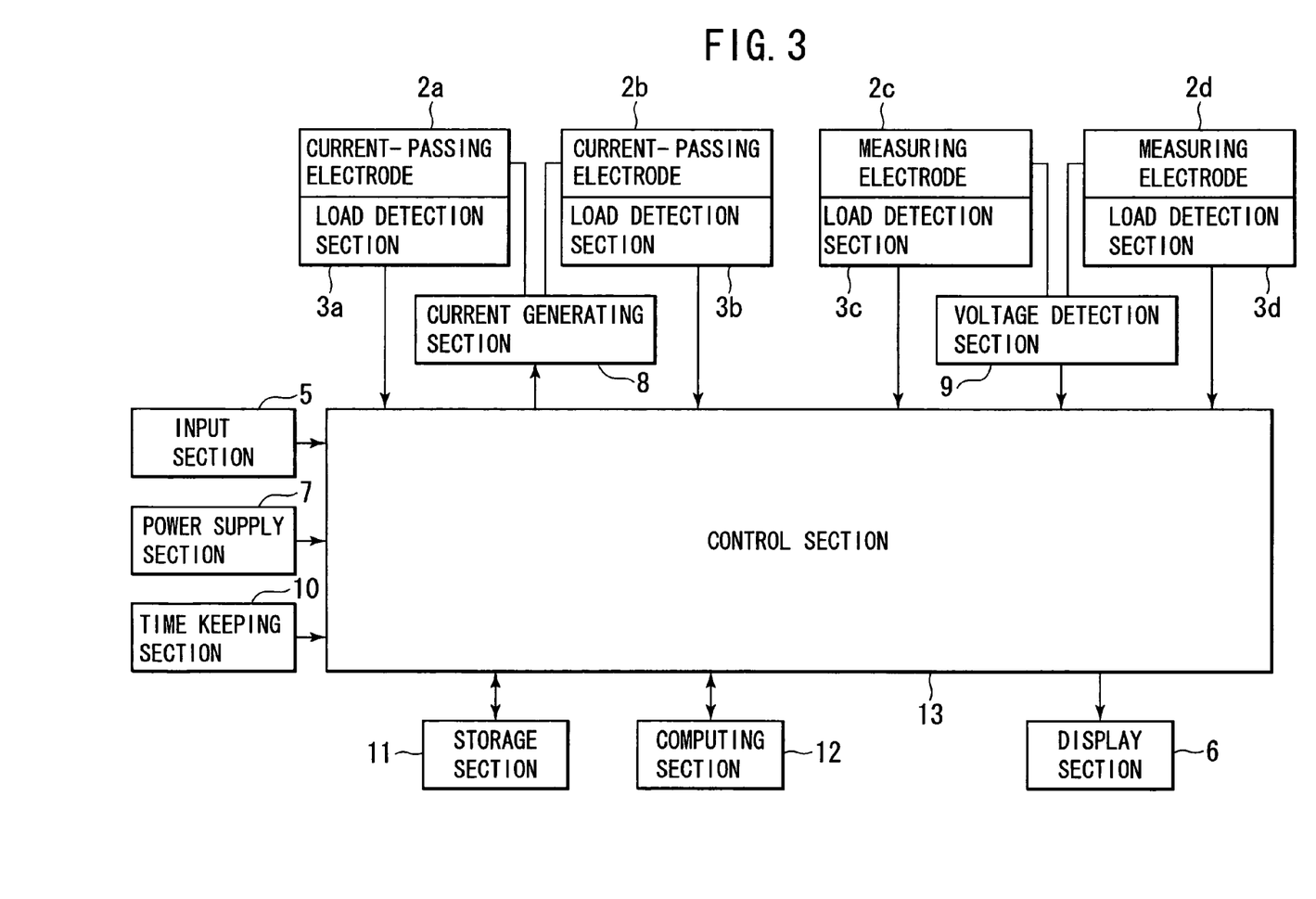
FIG. 3 is a block diagram illustrating the electrical configuration of the abdominal impedance based body composition meter according to the present invention.

First, the specific configuration of an abdominal impedance based body composition meter according to the present invention will be described by using primarily an external view shown in FIG. 1, a diagram shown in FIG. 2 illustrating the body composition meter during measurement, and a block diagram shown in FIG. 3.

The abdominal impedance based body composition meter according to the present invention is roughly constituted by a support 1, electrodes 2a, 2b, 2c and 2d, load sensing sections 3a, 3b, 3c and 3d, and an operation section 4.

The support 1 comprises a bar-shaped hollow body having a support surface 1c which is curved to fit the circumference of the abdomen. The bar-shaped hollow body also has grips 1a and 1b for keeping the support surface 1c pressed against an abdomen 100. The bar-shaped hollow body comprises a flexible material which is deformed such that the electrodes 2a, 2b, 2c and 2d can make closer contact with the surface of the abdomen 100 along the circumference of the abdomen when the support 1 is pressed against the abdomen.

The electrodes 2a and 2b are a pair of current-passing electrodes for passing a low-frequency current or high-frequency current through the abdomen 100. The electrodes 2c and 2d are a pair of measuring electrodes for detecting a potential difference which occurs in the abdomen 100 when a low-frequency current or high-frequency current is passed through the abdomen 100 from the current-passing electrodes 2a and 2b. The current-passing electrodes 2a and 2b are disposed on the load detection sections 3a and 3b which are disposed on the support surface 1c. The measuring electrodes 2c and 2d are disposed between the current-passing electrodes 2a and 2b and on the load detection sections 3c and 3d which are disposed on the support surface 1c. These electrodes are aligned in the abdominal circumferential direction.

The load detection sections 3a, 3b, 3c and 3d comprise a load sensor, an amplifier and an A/D converter. The load detection section 3a is disposed between the support 1 and the electrode 2a and detects a load signal when the electrode 2a is in contact with the abdomen 100. The load detection section 3b is disposed between the support 1 and the electrode 2b and detects a load signal when the electrode 2b is in contact with the abdomen 100. The load detection section 3c is disposed between the support 1 and the electrode 2c and detects a load signal when the electrode 2c is in contact with the abdomen 100. The load detection section 3d is disposed between the support 1 and the electrode 2d and detects a load signal when the electrode 2d is in contact with the abdomen 100.

The operation section 4 has an input section 5 and a display section 6 on an external surface of the case and has a power supply section 7, a current generating section 8, a voltage detection section 9, a time keeping section 10, a storage section 11, a computing section 12 and a control section 13 in the case. The operation section 4 is disposed on the support 1.

The power supply section 7 supplies electric power to each section in the electrical system of the present device. The time keeping section 10 keeps time. The input section 5 comprises a power switch 5a for starting supply of power from the power supply section 7 and a measurement switch 5b for starting measurements of an abdominal impedance and pressing force.

The current generating section 8 generates a current $A_{low}$ of low frequency (4 to 12.5 kHz (preferably 5 kHz)) to be passed through the abdomen 100 and a current $A_{high}$ of high frequency (128 to 512 kHz (preferably 256 kHz)) to be passed through the abdomen 100, under the control of the control section 13. The voltage detection section 9 detects a voltage $V_{low}$ which is generated between the measuring electrodes 2c and 2d when the low-frequency current $A_{low}$ is passed between the current-passing electrodes 2a and 2b and a voltage $V_{high}$ which is generated between the measuring electrodes 2c and 2d when the high-frequency current $A_{high}$ is passed between the current-passing electrodes 2a and 2b.

Further, the storage section 11 stores the following various arithmetic expressions (expressions (1) to (5)) for calculating body composition indicators (abdominal total fat area, subcutaneous fat area, visceral fat area, truncal fat percentage and total body fat percentage) based on an abdominal impedance $Z_{low}$ based on the voltage $V_{low}$ generated between the measuring electrodes $2c$ and $2d$, an abdominal impedance $Z_{high}$ based on the voltage $V_{high}$ generated between the measuring electrodes $2c$ and $2d$, a pressing force $SI_{avg}$ applied to the current-passing electrodes $2a$ and $2b$ and a pressing force $SV_{avg}$ applied to the measuring electrodes $2c$ and $2d$, input information, result information, programs and various other information.

$$\text{Abdominal Total Fat Area} = a \times Z_{low} + b \times Z_{high} + c \times SI_{avg} + d \times SV_{avg} \quad (1)$$

$$\text{Subcutaneous Fat Area} = e \times Z_{low} - f \times Z_{high} + g \times SI_{avg} + h \times SV_{avg} \quad (2)$$

$$\text{Visceral Fat Area} = -i \times Z_{low} + j \times Z_{high} + k \times SI_{avg} + m \times SV_{avg} \quad (3)$$

$$\text{Truncal Fat Percentage} = n - p \times 1 \div Z_{high} + q \times SI_{avg} + r \times SV_{avg} \quad (4)$$

$$\text{Total Body Fat Percentage} = s \times (n - p \times 1 \div Z_{high} + q \times SI_{avg} + r \times SV_{avg}) + t \quad (5)$$

In the expression (1), a, b, c and d are constants which provide a correlation with an abdominal total fat area determined by DXA (Dual X-ray Absorptiometry) which is a standard technique. In the expression (2), e, f, g and h are constants which provide a correlation with a subcutaneous fat area determined by DXA (Dual X-ray Absorptiometry) which is a standard technique. In the expression (3), i, j, k and m are constants which provide a correlation with a visceral fat area determined by DXA (Dual X-ray Absorptiometry) which is a standard technique. In the expression (4), n, p, q and r are constants which provide a correlation with a truncal fat percentage determined by DXA (Dual X-ray Absorptiometry) which is a standard technique. In the expression (5), s, n, p, q and r are constants which provide a correlation with a total body fat percentage determined by DXA (Dual X-ray Absorptiometry) which is a standard technique.

Figure 10:
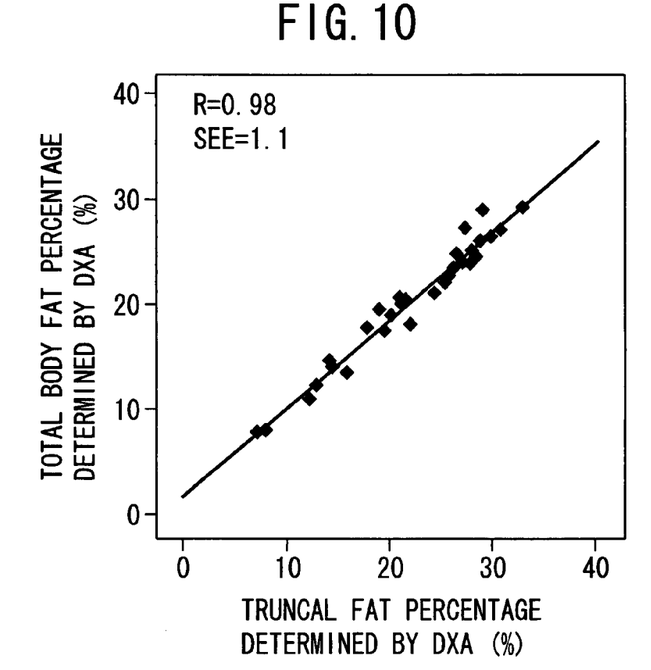
FIG. 10 is a graph illustrating the correlation between a total body fat percentage determined by DXA and a truncal fat percentage determined by DXA.

The abdominal total fat area, subcutaneous fat area, visceral fat area and truncal fat percentage determined by the above arithmetic expressions (expressions (1) to (4)) have high correlations with an abdominal total fat area, subcutaneous fat area, visceral fat area and truncal fat percentage determined by DXA (standard technique) which is generally considered to enjoy high estimation accuracy, as shown in FIGS. 6 to 9 (refer to R, SEE), and the truncal fat percentage determined by DXA (standard technique) which is generally considered to enjoy high estimation accuracy has a high correlation with a total body fat percentage determined by DXA, as shown in FIG. 10 (refer to R, SEE). Thus, the total body fat percentage determined by the above arithmetic expression (expression (5)) based on the truncal fat percentage has a high correlation with a total body fat percentage determined by DXA.

The computing section 12 (i) computes the abdominal impedance $Z_{low}$ based on the low-frequency current $A_{low}$ generated from the current generating section 8 and the voltage $V_{low}$ detected by the voltage detection section 9 upon passage of the current $A_{low}$, (ii) computes the abdominal impedance $Z_{high}$ based on the high-frequency current $A_{high}$ generated from the current generating section 8 and the voltage $V_{high}$ detected by the voltage detection section 9 upon passage of the current $A_{high}$, (iii) computes pressing forces SI1, SI2, SV1 and SV2 when the electrodes $2a$, $2b$, $2c$ and $2d$ are in contact with the abdomen 100 based on the load signals detected by the load detection sections $3a$, $3b$, $3c$ and $3d$ and computes the pressing force $SI_{avg}$ ($=(SI1+SI2) \div 2$) when the current-passing electrodes $2a$ and $2b$ are in contact with the abdomen 100 and the pressing force $SV_{avg}$ ($=(SV1+SV2) \div 2$) when the measuring electrodes $2c$ and $2d$ are in contact with the abdomen 100, (iv) computes body composition indicators (abdominal total fat area, subcutaneous fat area, visceral fat area, truncal fat percentage and total body fat percentage) by substituting the computed abdominal impedances $Z_{low}$ and $Z_{high}$ and pressing forces $SI_{avg}$ and $SV_{avg}$ into the arithmetic expressions (expressions (1) to (5)) stored in the storage section 11, and (v) computes various other data.

The display section 6 displays information about the results of computations of the body composition indicators (abdominal total fat area, subcutaneous fat area, visceral fat area, truncal fat percentage and total body fat percentage) by the computing section 12 as well as other input, measurement and result information.

The control section 13 (i) controls supply of power from the power supply section 7 to each section in the electrical system of the present device based on an ON signal from the power switch $5a$, (ii) controls generation of the low-frequency current $A_{low}$ and high-frequency current $A_{high}$ from the current generating section 8 based on an ON signal from the measurement switch $5b$, (iii) controls computations of the abdominal impedances $Z_{low}$ and $Z_{high}$ by the computing section 12 based on the voltages $V_{low}$ and $V_{high}$ generated between the measuring electrodes $2c$ and $2d$ from the voltage detection section 9, (iv) controls computations of the pressing forces SI1, SI2, SV1, SV2, $SI_{avg}$ and $SV_{avg}$ by the computing section 12 based on the detected signals from the load detection sections $3a$, $3b$, $3c$ and $3d$, (v) controls computations of the body composition indicators (abdominal total fat area, subcutaneous fat area, visceral fat area, truncal fat percentage and total body fat percentage) by the computing section 12, based on the abdominal impedances $Z_{low}$ and $Z_{high}$ computed by the computing section 12, the pressing forces $SI_{avg}$ and $SV_{avg}$ computed by the computing section 12 and the arithmetic expressions (expressions (1) to (5)) stored in the storage section 11, (vi) controls displaying of various input, measurement and result information by the display section 6 at input, measurement and result stages, and (vii) controls various other information.

Next, the principle of why the body composition indicators can be estimated by measuring the abdominal impedances and pressing forces will be described.

Figure 11:
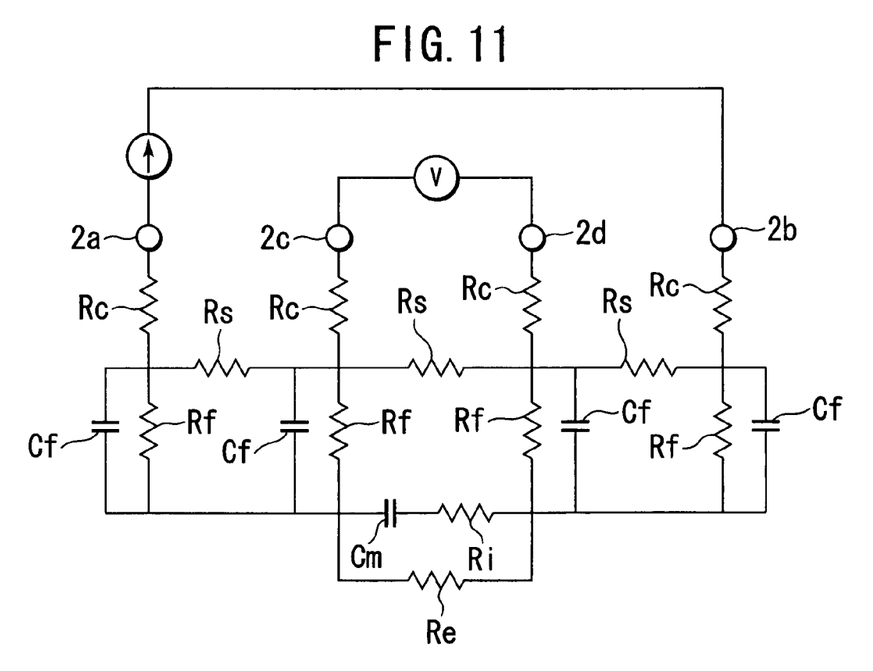
FIG. 11 is a diagram illustrating an electrical equivalent circuit model of the abdomen of a body.

As shown in a diagram illustrating an electrical equivalent circuit model of the abdomen of a body in FIG. 11, the superficial structure of the front section of the abdomen of a body can be represented by an electrical equivalent circuit model in which Rs represents a skin surface, Rf and Cf represent a subcutaneous fat layer, and Cm, Ri and Re represent a cell membrane, intracellular fluid and extracellular fluid in an abdominal muscle layer., respectively. Further, the state of measurement of abdominal impedance can be represented by an electrical equivalent circuit model having contact impedances Rc between the skin surface and electrodes (current-passing electrodes $2a$, $2b$, measuring electrodes $2c$, $2d$). When a low-frequency current (4 to 12.5 kHz (preferably 5 kHz)) is passed, the current does not pass through Cf and passes through only Rf in the subcutaneous fat layer, and the current does not pass through Cm (and therefore does not pass through Ri) and passes through only Re in the abdominal muscle layer, whereby an abdominal impedance reflecting the subcutaneous fat layer can be obtained. Meanwhile, when a high-frequency current (128 to 512 kHz (preferably 256 kHz)) is passed, the current passes through Cf (and therefore does not pass through Rf) in the subcutaneous fat layer, and the current passes through Cm, Ri and Re in the abdominal muscle layer, whereby an abdominal impedance reflecting the abdominal muscle layer (abdominal impedance which reflects visceral fat tissues due to thinly spread abdominal muscles caused by large accumulation of visceral fat) can be obtained.

Figure 12:
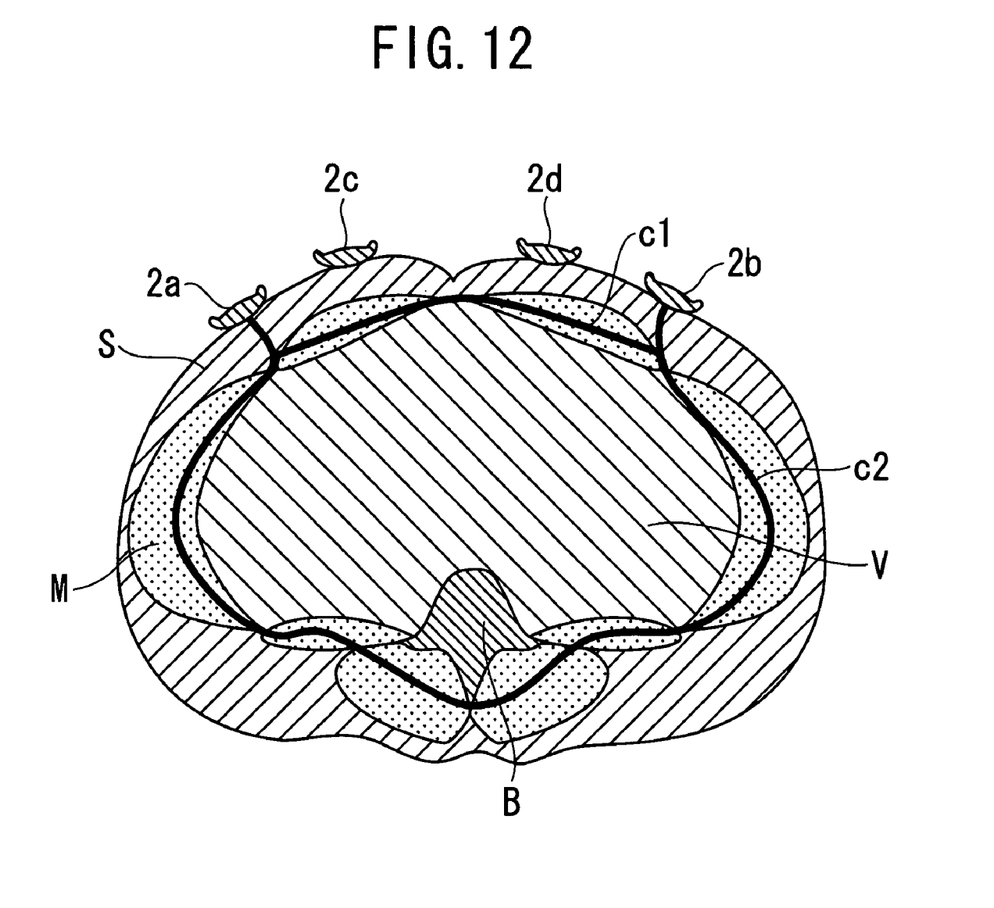
FIG. 12 is a diagram illustrating current pathways in the abdomen of a body.

Further, when a current is passed from the current-passing electrodes 2a and 2b with the electrodes 2a, 2b, 2c and 2d in contact with the front section of the abdomen, the current passes through the abdominal muscle layer on the abdomen side and the abdominal muscle layer on the back side as pathways (c1, c2), as shown in an abdomen cross-section diagram in FIG. 12 illustrating current pathways (in FIG. 12, S represents subcutaneous fat, V represents splanchnic organs and visceral fat, M represents muscles, B represents the backbone). Since the state of deformation of the abdomen 100 varies according to a force pressing the electrodes 2a, 2b, 2c and 2d against the abdomen 100, the skin surface Rs, subcutaneous fat layers Rf and Cf and abdominal muscle layer (cell membrane Cm, intracellular fluid Ri, extracellular fluid Re) also vary.

Accordingly, body composition indicators (abdominal total fat area, subcutaneous fat area, visceral fat area, truncal fat percentage, total body fat percentage) can be estimated by combining the abdominal impedances $Z_{low}$ and $Z_{high}$ and pressing forces $SI_{avg}$ and $SV_{avg}$ as appropriate as in the arithmetic expressions (expressions (1) to (5)).

In the above description, the power supply section 7, support 1, current-passing electrodes 2a and 2b, measuring electrodes 2c and 2d, current generating section 8, voltage detection section 9, computing section 12 and control section 13 constitute abdominal impedance measuring means. Further, the power supply section 7, load detection sections 3a, 3b, 3c and 3d, computing section 12 and control section 13 constitute pressing force measuring means. Further, the power supply section 7, storage section 11, computing section 12 and control section 13 constitute body composition estimating means.

Figure 4:
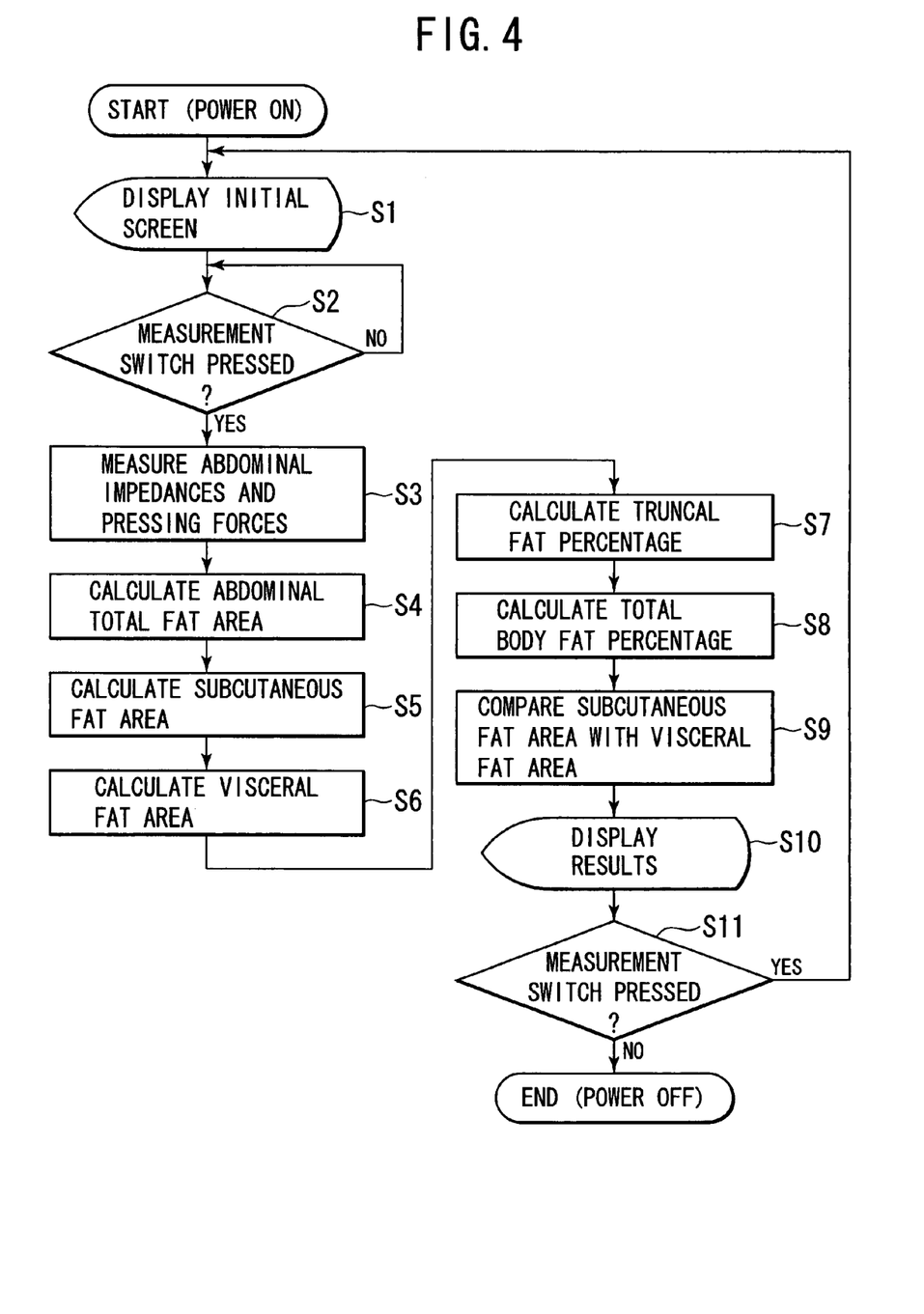
FIG. 4 is a flowchart illustrating the operational procedures of the abdominal impedance based body composition meter according to the present invention.

Next, the operation of an abdominal impedance based body composition meter according to the present invention will be described by using primarily a flowchart shown in FIG. 4.

Figure 5A:
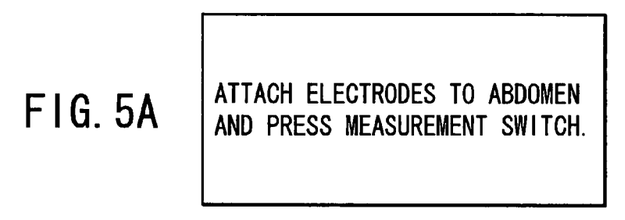
FIG. 5 shows screen images displayed between the start and the end of measurement.

First, when the power switch 5a is pressed, power is supplied from the power supply section 7 to each section in the electrical system, and such an initial screen as shown in FIG. 5A is displayed in the display section 6 (STEP S1).

Then, the control section 13 determines whether the measurement switch 5b has been pressed (STEP S2). If the measurement switch 5b has not been pressed (NO in STEP S2), the control section 13 repeats the process of this measurement standby state until the measurement switch 5b is pressed.

Figure 5B:
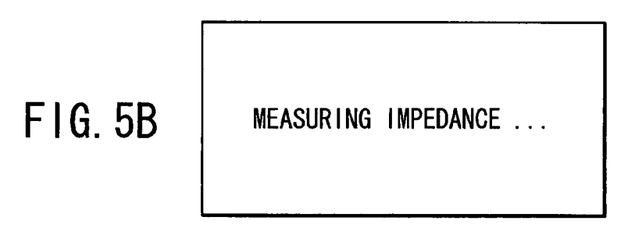

Meanwhile, when the measurement switch 5b is pressed with the support surface 1c having the electrodes 2a, 2b, 2c and 2d disposed thereon of the support 1 pressed against the front section of the abdomen as shown in FIG. 2 (YES in STEP S2), the present device operates as follows. That is, under the control of the control section 13, (i) the current generating section 8 generates a current $A_{low}$ of low frequency (4 to 12.5 kHz (preferably 5 kHz)) between the current-passing electrodes 2a and 2b, the voltage detection section 9 detects a voltage $V_{low}$ which is generated between the measuring electrodes 2c and 2d upon generation of the current $A_{low}$, and the computing section 12 computes an abdominal impedance $Z_{low}$ based on the generated low-frequency current $A_{low}$ and the detected voltage $V_{low}$, (ii) the current generating section 8 generates a current $A_{high}$ of high frequency (128 to 512 kHz (preferably 256 kHz)) between the current-passing electrodes 2a and 2b, the voltage detection section 9 detects a voltage $V_{high}$ which is generated between the measuring electrodes 2c and 2d upon generation of the current $A_{high}$, and the computing section 12 computes an abdominal impedance $Z_{high}$ based on the generated high-frequency current $A_{high}$ and the detected voltage $V_{high}$, (iii) load signals when the electrodes 2a, 2b, 2c and 2d are in contact with the abdomen are detected, and the computing section 12 computes pressing forces SI1, SI2, SV1 and SV2 when the electrodes 2a, 2b, 2c and 2d are in contact with the abdomen based on the detected load signals, computes a pressing force $SI_{avg}$ when the current-passing electrodes 2a and 2b are in contact with the abdomen based on these computed SI1 and SI2 by $SI_{avg}=(SI1+SI2)\div 2$ and computes a pressing force $SV_{avg}$ when the measuring electrodes 2c and 2d are in contact with the abdomen based on these computed SV1 and SV2 by $SV_{avg}=(SV1+SV2)\div 2$, and (iv) the storage section 11 temporarily stores these computed abdominal impedances $Z_{low}$ and $Z_{high}$ and pressing forces $SI_{avg}$ and $SV_{avg}$ (STEP S3). During measurement of the abdominal impedances, the display section 6 displays such a message as shown in FIG. 5B.

Then, under the control of the control section 13, the computing section 12 computes an abdominal total fat area by substituting the abdominal impedances $Z_{low}$ and $Z_{high}$ and pressing forces $SI_{avg}$ and $SV_{avg}$ which are temporarily stored in the storage section 11 into the arithmetic expression (1) which is stored in the storage section 11, and the storage section 11 temporarily stores the computed abdominal total fat area (STEP S4).

Then, under the control of the control section 13, the computing section 12 computes a subcutaneous fat area by substituting the abdominal impedances $Z_{low}$ and $Z_{high}$ and pressing forces $SI_{avg}$ and $SV_{avg}$ which are temporarily stored in the storage section 11 into the arithmetic expression (2) which is stored in the storage section 11, and the storage section 11 temporarily stores the computed subcutaneous fat area (STEP S5).

Then, under the control of the control section 13, the computing section 12 computes a visceral fat area by substituting the abdominal impedances $Z_{low}$ and $Z_{high}$ and pressing forces $SI_{avg}$ and $SV_{avg}$ which are temporarily stored in the storage section 11 into the arithmetic expression (3) which is stored in the storage section 11, and the storage section 11 temporarily stores the computed visceral fat area (STEP S6).

Then, under the control of the control section 13, the computing section 12 computes a truncal fat percentage by substituting the abdominal impedance $Z_{high}$ and pressing forces $SI_{avg}$ and $SV_{avg}$ which are temporarily stored in the storage section 11 into the arithmetic expression (4) which is stored in the storage section 11, and the storage section 11 temporarily stores the computed truncal fat percentage (STEP S7).

Then, under the control of the control section 13, the computing section 12 computes a total body fat percentage by substituting the abdominal impedance $Z_{high}$ and pressing forces $SI_{avg}$ and $SV_{avg}$ which are temporarily stored in the storage section 11 into the arithmetic expression (5) which is stored in the storage section 11, and the storage section 11 temporarily stores the computed total body fat percentage (STEP S8).

Figure 5C:
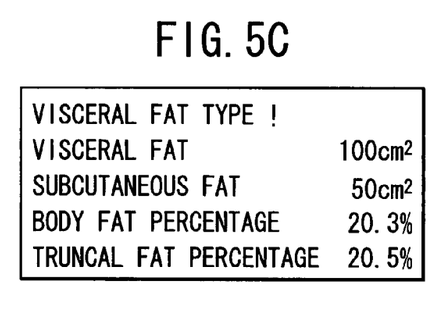
Figure 5D:
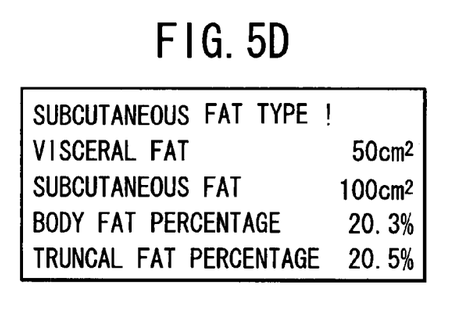
Figure 5E:
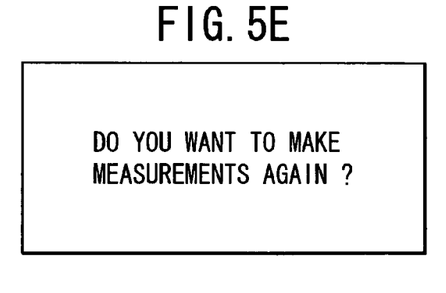
Figure 6:
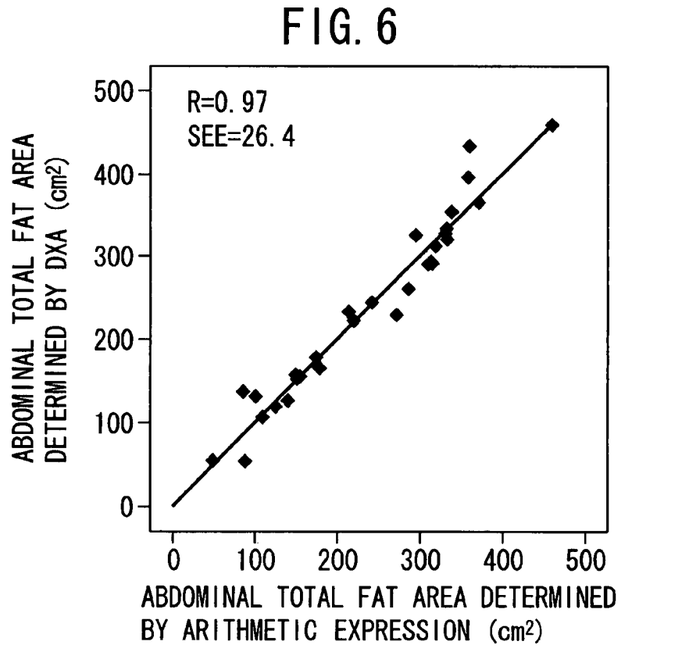
FIG. 6 is a graph illustrating the correlation between an abdominal total fat area determined by DXA and an abdominal total fat area determined by an arithmetic expression.
Figure 7:
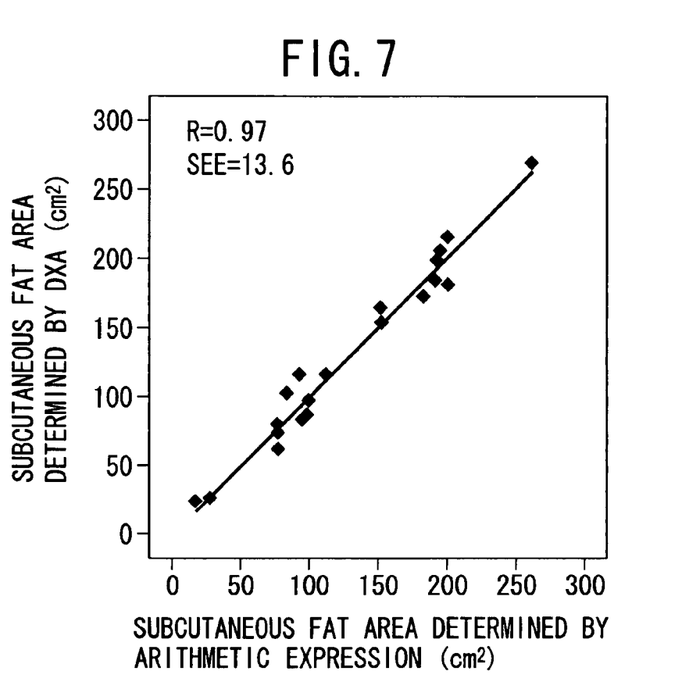
FIG. 7 is a graph illustrating the correlation between a subcutaneous fat area determined by DXA and a subcutaneous fat area determined by an arithmetic expression.
Figure 8:
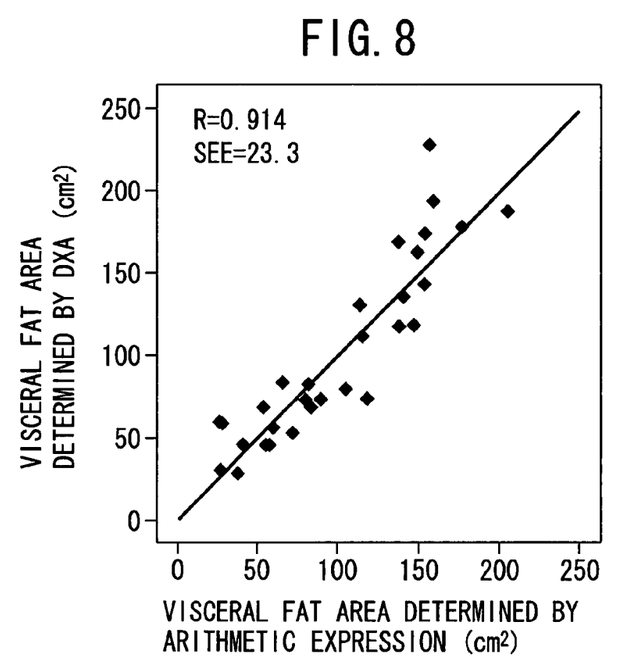
FIG. 8 is a graph illustrating the correlation between a visceral fat area determined by DXA and a visceral fat area determined by an arithmetic expression.
Figure 9:
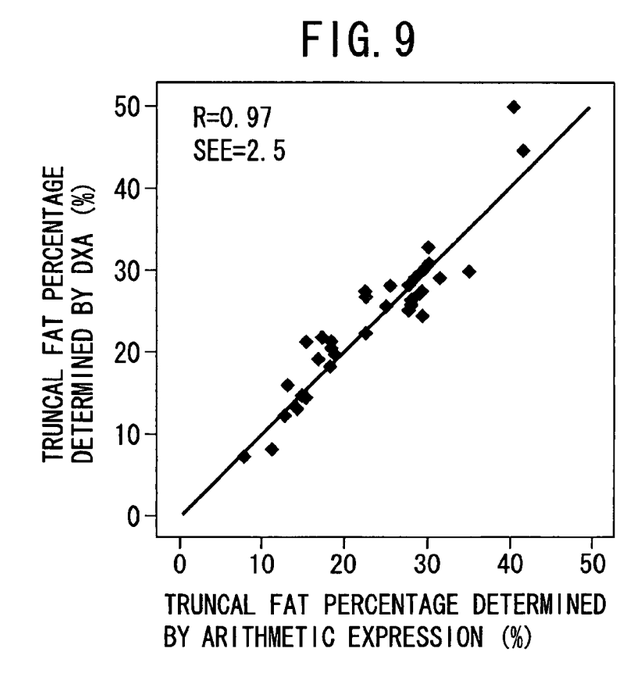
FIG. 9 is a graph illustrating the correlation between a truncal fat percentage determined by DXA and a truncal fat percentage determined by an arithmetic expression.

Then, under the control of the control section 13, the computing section 12 compares the subcutaneous fat area with visceral fat area which are temporarily stored in the storage section 11 (STEP S9). When the result of the comparison is visceral fat area—subcutaneous fat area$\geq 0$, the display section 6 displays the measurement results with a message "Visceral Fat Type !" as shown in FIG. 5C, while when it is not visceral fat area—subcutaneous fat area$\geq 0$, the display section 6 displays the measurement results with a message "Subcutaneous Fat Type !" as shown in FIG. 5D. In either case, the display section 6 displays the measurement results and the message for a given period of time and then displays a screen inquiring about remeasurements as shown in FIG. 5E (STEP S10).

Then, the control section 13 determines whether the measurement switch 5b has been pressed (STEP S11). When the measurement switch 5b has been pressed (YES in STEP S11), the present device returns to the initial screen (STEP S1), thereby making it possible to carry out a series of the above measurement steps. Meanwhile, when the measurement switch 5b has not been pressed for a given period of time kept by the time keeping section 10 (NO in STEP S11), the power is turned off automatically, thereby ending a series of operations.

According to the thus constituted abdominal impedance based body composition meter of the above example, even if the degree of force pressing the support 1 against the abdomen varies and the degree of deformation of the abdomen by the electrodes 2a, 2b, 2c and 2d varies, body composition indicators (abdominal total fat area, subcutaneous fat area, visceral fat area, truncal fat percentage, total body fat percentage) can be estimated with high accuracy, because the body composition indicators are calculated by use of the arithmetic expressions (expressions (1) to (5)) which take the pressing forces $SI_{avg}$ and $SV_{avg}$ into consideration and have high correlations with body composition indicators determined by DXA.

Although the arithmetic expressions (expressions (1) to (5)) having high correlations with body composition indicators determined by DXA are used in the above example, arithmetic expressions having high correlations with body composition indicators determined by a technique which is generally considered to enjoy high estimation accuracy such as CT (Computed Tomography) may be used. Comparable estimation accuracy can be obtained for body composition indicators.

What is claimed is:

1. An abdominal impedance based body composition meter comprising:
   abdominal impedance measuring means;
   pressing force measuring means; and
   body composition estimating means;
   wherein the abdominal impedance measuring means comprises a plurality of electrodes and a support which keeps the electrodes pressed against the abdomen and measures an abdominal impedance when the electrodes are in contact with the abdomen,
   wherein the pressing force measuring means measures a pressing force when the electrodes are pressed against the abdomen by the support,
   wherein the body composition estimating means estimates a body composition indicator based on the abdominal impedance measured by the abdominal impedance measuring means and the pressing force measured by the pressing force measuring means,
   wherein the electrodes comprise a pair of current-passing electrodes and a pair of measuring electrodes,
   wherein the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections,
   wherein the abdominal impedance measuring means determines an abdominal impedance based on a potential difference which is detected between the measuring electrodes when a low-frequency current is passed between the current-passing electrodes and determines an abdominal impedance based on a potential difference which is detected between the measuring electrodes when a high-frequency current is passed between the current-passing electrodes, and determines an additional abdominal impedance,
   wherein the body composition estimating means computes and estimates an abdominal total fat area as the body composition indicator by substituting the abdominal impedance determined by the abdominal impedance measuring means by passing the low-frequency current into $Z_{low}$, the additional abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$, and constants which provide a correlation with an abdominal total fat area determined by a standard technique into a, b, c and d, in an arithmetic expression represented by abdominal total fat area=$a \times Z_{low} + b \times Z_{high} + c \times SI_{avg} + d \times SV_{avg}$.

2. An abdominal impedance based body composition meter comprising:
   abdominal impedance measuring means;
   pressing force measuring means; and
   body composition estimating means;
   wherein the abdominal impedance measuring means comprises a plurality of electrodes and a support which keeps the electrodes pressed against the abdomen and measures an abdominal impedance when the electrodes are in contact with the abdomen,
   wherein the pressing force measuring means measures a pressing force when the electrodes are pressed against the abdomen by the support,
   wherein the body composition estimating means estimates a body composition indicator based on the abdominal impedance measured by the abdominal impedance measuring means and the pressing force measured by the pressing force measuring means,
   wherein the electrodes comprise a pair of current-passing electrodes and a pair of measuring electrodes,
   wherein the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections,
   wherein the abdominal impedance measuring means determines an abdominal impedance based on a potential difference which is detected between the measuring electrodes when a low-frequency current is passed between the current-passing electrodes, and determines an additional abdominal impedance based on a potential difference which is detected between the measuring electrodes when a high-frequency current is passed between the current-passing electrodes, and
   wherein the body composition estimating means computes and estimates a subcutaneous fat area as the body composition indicator by substituting the abdominal impedance determined by the abdominal impedance measuring means by passing the low-frequency current into $Z_{low}$, the additional abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$, and constants which provide a correlation with a subcutaneous fat area determined by a standard technique into e, f, g and h, in an arithmetic expression represented by subcutaneous fat area $= e \times Z_{low} - f \times Z_{high} + g \times SI_{avg} + h \times SV_{avg}$.

3. An abdominal impedance based body composition meter comprising:
   abdominal impedance measuring means;
   pressing force measuring means; and
   body composition estimating means;
   wherein the abdominal impedance measuring means comprises a plurality of electrodes and a support which keeps the electrodes pressed against the abdomen and measures an abdominal impedance when the electrodes are in contact with the abdomen,
   wherein the pressing force measuring means measures a pressing force when the electrodes are pressed against the abdomen by the support,
   wherein the body composition estimating means estimates a body composition indicator based on the abdominal impedance measured by the abdominal impedance measuring means and the pressing force measured by the pressing force measuring means,
   wherein the electrodes comprise a pair of current-passing electrodes and a pair of measuring electrodes,
   wherein the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections,
   wherein the abdominal impedance measuring means determines an abdominal impedance based on a potential difference which is detected between the measuring electrodes when a low-frequency current is passed between the current-passing electrodes and determines an abdominal impedance based on a potential difference which is detected between the measuring electrodes when a high-frequency current is passed between the current-passing electrodes, and determines an
   wherein the body composition estimating means computes and estimates a visceral fat area as the body composition indicator by substituting the abdominal impedance determined by the abdominal impedance measuring means by passing the low-frequency current into $Z_{low}$, the additional abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$, and constants which provide a correlation with a visceral fat area determined by a standard technique into i, j, k, and m, in an arithmetic expression represented by visceral fat area $= -i \times Z_{low} + j \times Z_{high} + k \times SI_{avg} + m \times SV_{avg}$.

4. An abdominal impedance based body composition meter comprising:
   abdominal impedance measuring means;
   pressing force measuring means; and
   body composition estimating means;
   wherein the abdominal impedance measuring means comprises a plurality of electrodes and a support which keeps the electrodes pressed against the abdomen and measures an abdominal impedance when the electrodes are in contact with the abdomen,
   wherein the pressing force measuring means measures a pressing force when the electrodes are pressed against the abdomen by the support,
   wherein the body composition estimating means estimates a body composition indicator based on the abdominal impedance measured by the abdominal impedance measuring means and the pressing force measured by the pressing force measuring means,
   wherein the electrodes comprise a pair of current-passing electrodes and a pair of measuring electrodes,
   wherein the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections,
   wherein the abdominal impedance measuring means determines an abdominal impedance based on a potential difference which is detected between the measuring electrodes when a high-frequency current is passed between the current-passing electrodes, and
   wherein the body composition estimating means computes and estimates a truncal fat percentage as the body composition indicator by substituting the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$, and constants and which provide a correlation with a truncal fat percentage determined by a standard technique into n, p, q and r, in an arithmetic expression represented by truncal fat percentage $= n - p \times 1 \div Z_{high} + q \times SI_{avg} + r \times SV_{avg}$.

5. An abdominal impedance based body composition meter comprising:
   abdominal impedance measuring means;
   pressing force measuring means; and
   body composition estimating means;
   wherein the abdominal impedance measuring means comprises a plurality of electrodes and a support which keeps the electrodes pressed against the abdomen and measures an abdominal impedance when the electrodes are in contact with the abdomen,
   wherein the pressing force measuring means measures a pressing force when the electrodes are pressed against the abdomen by the support,
   wherein the body composition estimating means estimates a body composition indicator based on the abdominal impedance measured by the abdominal impedance measuring means and the pressing force measured by the pressing force measuring means,
   wherein the electrodes comprise a pair of current-passing electrodes and a pair of measuring electrodes, wherein the pressing force measuring means comprises load detection sections which detect loads produced when the electrodes are pressed against the abdomen and determines a pressing force applied to the current-passing electrodes and a pressing force applied to the measuring electrodes based on the loads detected by the load detection sections, wherein the abdominal impedance measuring means determines an abdominal impedance based on a potential difference which is detected between the measuring electrodes when a high-frequency current is passed between the current-passing electrodes, and wherein the body composition estimating means computes and estimates a total body fat percentage as the body composition indicator by substituting the abdominal impedance determined by the abdominal impedance measuring means by passing the high-frequency current into $Z_{high}$, the pressing force applied to the current-passing electrodes which has been determined by the pressing force measuring means into $SI_{avg}$, the pressing force applied to the measuring electrodes which has been determined by the pressing force measuring means into $SV_{avg}$, and constants which provide a correlation with a total body fat percentage determined by a standard technique into n, p, q, r, s and t, in an arithmetic expression represented by total body fat percentage $=s \times (n-p \times 1 \div Z_{high}+q \times SI_{avg}+r \times SV_{avg})+t$.

* * * * *